(12) United States Patent
Kinsman et al.

(10) Patent No.: US 9,688,444 B2
(45) Date of Patent: Jun. 27, 2017

(54) SINGLE USE CONTAINER WITH DISPENSER

(71) Applicant: R.P. Scherer Technologies, LLC, Las Vegas, NV (US)

(72) Inventors: Sean Thomas Kinsman, Cherry Valley, IL (US); Timothy Scott Hansen, Woodstock, IL (US); Kevin Colin Colangelo, Fox Lake, IL (US)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 50 days.

(21) Appl. No.: 14/441,783

(22) PCT Filed: Nov. 13, 2013

(86) PCT No.: PCT/US2013/069781
§ 371 (c)(1),
(2) Date: May 8, 2015

(87) PCT Pub. No.: WO2014/081592
PCT Pub. Date: May 30, 2014

(65) Prior Publication Data
US 2015/0307237 A1    Oct. 29, 2015

Related U.S. Application Data

(60) Provisional application No. 61/728,836, filed on Nov. 21, 2012.

(51) Int. Cl.
*B43K 5/14* (2006.01)
*B65D 35/36* (2006.01)
(Continued)

(52) U.S. Cl.
CPC ........... *B65D 35/36* (2013.01); *A61M 35/003* (2013.01); *A61M 35/006* (2013.01); *B65D 1/32* (2013.01);
(Continued)

(58) Field of Classification Search
CPC ..... A61M 35/003; A61M 35/006; B65D 1/32; B65D 35/36; B65D 47/42; B65D 51/222
(Continued)

(56) References Cited

U.S. PATENT DOCUMENTS

| 4,921,137 A | 5/1990 | Heijenga |
| 5,042,690 A | 8/1991 | O'Meara |

(Continued)

FOREIGN PATENT DOCUMENTS

| CN | 101723124 A | 6/2010 |
| JP | 05504319 A | 7/1993 |

(Continued)

OTHER PUBLICATIONS

English Translation of Chinese Office Action; Mailed Apr. 19, 2016 for CN Application No. CN201380060926.3.
(Continued)

*Primary Examiner* — Jennifer C Chiang
(74) *Attorney, Agent, or Firm* — Mendelsohn Dunleavy, P.C.

(57) ABSTRACT

Single use containers designed to store and dispense liquid substances having a wide variation in viscosities. The container includes a container body that defines a storage compartment for storing the liquid substance and is provided with a neck including a seal positioned in the neck to seal a liquid substance in the storage compartment during storage. The container also includes a cap defining a recess and being adapted for engaging the neck and including structure for piercing the seal and a channel which passes through the
(Continued)

structure for piercing the seal to the recess. An applicator is located in the recess such that the applicator and recess together define a chamber between an end of the channel and the applicator to allow liquid to flow from said channel into said chamber.

18 Claims, 5 Drawing Sheets

(51) Int. Cl.
  *A61M 35/00* (2006.01)
  *A61F 13/40* (2006.01)
  *B65D 23/10* (2006.01)
  *B65D 1/32* (2006.01)
  *B65D 47/42* (2006.01)
  *B65D 51/22* (2006.01)
  *B65D 35/44* (2006.01)

(52) U.S. Cl.
  CPC .......... *B65D 23/102* (2013.01); *B65D 35/44* (2013.01); *B65D 47/42* (2013.01); *B65D 51/222* (2013.01)

(58) Field of Classification Search
  USPC .................................. 401/133, 134
  See application file for complete search history.

(56) References Cited

U.S. PATENT DOCUMENTS

| | | | |
|---|---|---|---|
| D363,377 S | 10/1995 | Koptis | |
| 5,577,851 A | 11/1996 | Koptis | |
| 6,007,264 A | 12/1999 | Koptis | |
| 6,117,123 A | 9/2000 | Barney et al. | |
| 6,805,512 B2 * | 10/2004 | King .................... | A45D 34/045 401/133 |
| 6,902,335 B2 | 6/2005 | Bergey et al. | |
| 6,929,152 B2 * | 8/2005 | Bonningue ............ | B65D 47/20 222/82 |
| 7,572,079 B2 * | 8/2009 | Wong ................. | A46B 11/0041 222/83 |
| 8,109,236 B2 * | 2/2012 | Brodowski ............ | A01N 25/34 119/71 |
| 2002/0190087 A1 | 12/2002 | Vakiener et al. | |
| 2004/0074925 A1 | 4/2004 | Faurie | |
| 2006/0037972 A1 | 2/2006 | Leiner et al. | |
| 2006/0163190 A1 | 7/2006 | Laveault et al. | |
| 2011/0297703 A1 | 12/2011 | Wilson et al. | |

FOREIGN PATENT DOCUMENTS

| | | |
|---|---|---|
| JP | 2002517358 A | 6/2002 |
| JP | 2011105336 A | 6/2011 |
| WO | WO9112197 A1 | 8/1991 |
| WO | WO9963934 A2 | 12/1999 |

OTHER PUBLICATIONS

International Preliminary Report on Patentability and Written Opinion; Mailed Jun. 4, 2015 for the corresponding PCT Application No. PCT/US2013/069781.

European Search Report; Mailed Jul. 8, 2015 for the corresponding EP Application No. EP13856579.1.

Japanese Office Action; mailed Jan. 17, 2017 for JP Application No. JP2015-542734.

* cited by examiner

SINGLE USE CONTAINER WITH DISPENSER

BACKGROUND OF THE INVENTION

1. Field of the Invention

The present invention relates to single use containers including applicator. In particular, the present invention is directed to blow-fill-sealed single use containers for storing and dispensing a fluid substance.

2. Description of the Related Technology

Measured amounts of various fluid substances are commonly dispensed in relatively small packages, often for single use. The fluids include a wide variety of products, including food products such as condiments, personal care products such as shampoos and skin creams, cleaning products such as various packaged "wipes," and pharmaceutical products such as medications.

A popular package is a single serving package formed from two sheets of foil or plastic, superimposed over one another and sealed together around the periphery. The package has a notch or other means to facilitate tearing one edge away from the container. The user tears open the container, dispenses the fluid, and disposes of the container. One such example is a single serving ketchup package.

Such packages, while relatively simple and inexpensive, have several drawbacks. First, the package contains no means for directing or spreading the dispensed fluid. In particular, thick fluids tend to be dispensed from this type of package as a bolus, leaving the user to find a way to spread the bolus. Alternatively, thin fluids tend to be dispensed from this type of package in a difficult to control stream.

Second, this type of package can be quite difficult to open, particularly for those with arthritic hands or otherwise compromised grip strength. This difficulty is at least in part caused by the fact that, in the conventional designs of this package, it is necessary to tear away one of the sidewalls of the package in order to release the contents. However, the same sidewall must be sufficiently strong to contain the contents of the package under normal handling conditions, which may include accidental compression. Even a small amount of moisture or skin oil on the surface of the package can make gripping and tearing the strong sidewall quite difficult. Frustrated users often use their teeth to open ostensibly manually "tear open" packages, presenting aesthetic and hygienic issues.

Third, the velocity of the fluid as it is expelled from the package varies with the viscosity of the fluid, the amount of sidewall opened and the pressure applied. When the package has only a pinpoint opening in its side, a relatively strong squeeze on the package can propel the low viscosity fluid within the package to quite some distance. This can create a nuisance for the user.

Improvements on various aspects of this type of package have been proposed. U.S. Pat. No. 5,577,851 discloses a sponge applicator attached to a tube dispenser that contains a quantity of a substance, such as painter's spackle, to be dispensed. After use, the sponge applicator is designed to be removed, cleaned, and returned to the tube dispenser. The reuse of the sponge applicator raises issues of potential hardening and chemical or bacterial deterioration of the sponge. This applicator is unsuitable for use with products such as those intended for human consumption, where reuse of the applicator may cause bacterial contamination. U.S. Pat. No. D363,377 similarly discloses an integral spreader, which provides a roller atop a dispensing container. The roller spreads the dispensed fluid, but is subject to the same cleaning and hygienic drawbacks.

Efforts to produce an integral spreading means suitable for single use containers have achieved mixed success. For example, U.S. Pat. No. 6,007,264 discloses a package comprising two superimposed sheets sealed together around their periphery, with the provision of peelable flaps along one edge of the package. The user peels back the flaps, pulling apart one sealed edge of the package and thus exposing the contents. The peeled back flaps, at an approximate 90-degree angle to the package, thereby provide a butterfly wing type spreader for spreading the contents. Such a design overcomes any need to clean or re-use the spreading device, as the entire package is disposable after use.

However, the successful implementation of this type of package depends largely on the viscosity of the fluid dispensed. For example, fluids with a high viscosity, such as ketchup or heavy creams, tend to be dispensed as a discrete bolus, whereupon they can be effectively smeared about the intended surface by the butterfly wings. When used with liquids of low fluid viscosity, such as some pharmaceutical preparations and other relatively thin liquids, such fluids tend to be dispensed from the opened package in a stream, as opposed to a bolus, and thus the fluids tend to run out of the flap or wing spreading area before they can be effectively spread.

To counter this undesirable propensity, the same patent discloses embodiments wherein an absorbent foam applicator is either applied in two pieces to the opposing flaps or is applied in a single piece bridging the flaps. Such embodiments are designed to provide an absorbent surface area to facilitate the spreading of the dispensed fluid. However, this design has achieved only marginal success because the separate foam applicators are ineffective in retarding the sudden flow of the fluid from the ruptured packaging.

U.S. Pat. No. 4,921,137 discloses a container with an enlarged ear-like structure that facilitates grip, including a channel portion within the ear-like structure to minimize the sudden gushing of contained substance under pressure, especially for substances with low viscosity. However, the container does not include any means for spreading a bolus of dispensed liquid.

U.S. Pat. No. 6,117,123 discloses a flexible container that provides for the storage and mixing of diluents and medicaments. The container incorporates multiple compartments, separated by preferentially peelable seals, in which the diluents and medicaments are stored. The peelable seals are ruptured by manipulation of the container to thereby mix the components together for delivery through standard I.V. equipment to a patient. The seals are constructed such that the seal between the diluent and medicament compartments is preferentially ruptured to allow the liquid medicament and diluent to be mixed before the combined solution is accessible for administration.

U.S. Pat. No. 6,902,335 discloses a dispensing container including a compartment, a chamber, and an applicator pad. The chamber and the compartment may be fabricated out of separate materials that are bonded together. It is preferred, however, that the chamber and the compartment be fabricated from the same material as a single structure separated into two sections by a frangible seal. The container is designed to contain a flowable substance that can be dispensed by applying pressure upon the compartment area, where the substance is stored. The pressure ruptures the frangible seal and expresses the substance into the chamber, behind the applicator. The expansion of the chamber walls and the resilience of the applicator pad allow the substance to spread out behind and into the applicator, where it is available to be expelled and applied. This container is suitable for high viscosity substances but substances with low viscosity may still be suddenly expelled through the applicator, when the pressure exerted on the compartment is not adequately controlled.

Thus, there remains a need for single-use containers that are sufficiently versatile to allow for dispensing of both high and low viscosity substances and which facilitate simple even spreading of the dispensed liquid substance.

SUMMARY OF THE INVENTION

The present invention is directed to a single-use container designed to store and dispense a liquid substance. The container includes a container body for storing the liquid substance. The container body defines a storage compartment and a neck and includes a frangible seal. The container also includes a cap adapted to engage the container body and including structure for piercing the frangible seal. The cap also includes an upper portion that defines a recess and a channel through which fluid is passed when during dispensing. The container also includes an applicator positioned in the recess of the cap such that fluid passed through the channel encounters the applicator as it is dispensed.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

While this invention is susceptible of embodiments in many different forms, there is shown in the drawings and will herein be described in detail one specific embodiment of the invention, with the understanding that the present disclosure is to be considered as an exemplification of the principles of the invention and is not intended to limit the invention to the embodiment as illustrated. The precise shapes and sizes of the components herein described are not essential to the invention unless otherwise indicated, since the invention is described with reference to an illustrative embodiment only.

For ease of description, the invention will be described with the body of the container of this invention standing upright on a surface, and terms such as upper, lower, horizontal, etc., will be used with reference to this position. It will be understood, however, that the container may be manufactured, transported, stored, and sold in an orientation other than that illustrated.

Figure 1:
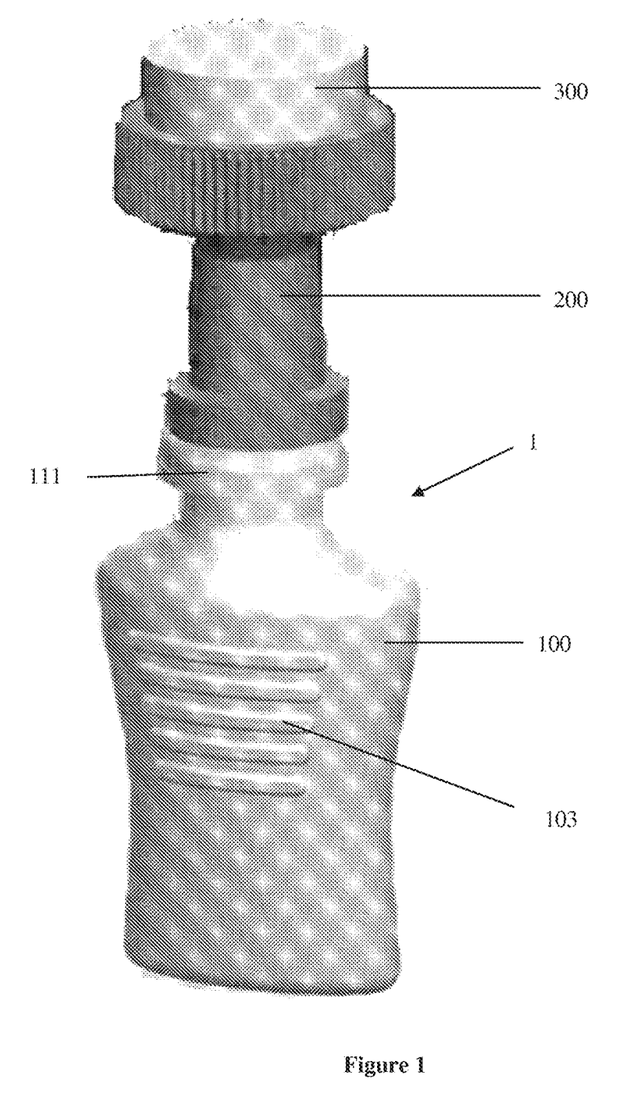
FIG. 1 depicts a container with dispenser according to an embodiment of the present invention.

The present invention relates to a single-use container 1 provided with a dispenser. Referring to FIG. 1, the container 1 includes a container body 100, a cap 200 and an applicator 300. The container of the present invention may be fabricated by, for example, a blow-fill-seal seal process. In such a process, the container 1 is first blow molded to define a storage compartment. Then, the storage compartment of container 1 is filled with a liquid material. Finally, the filled container 1 is sealed to thereby seal the liquid material within the storage compartment.

Figure 2A:
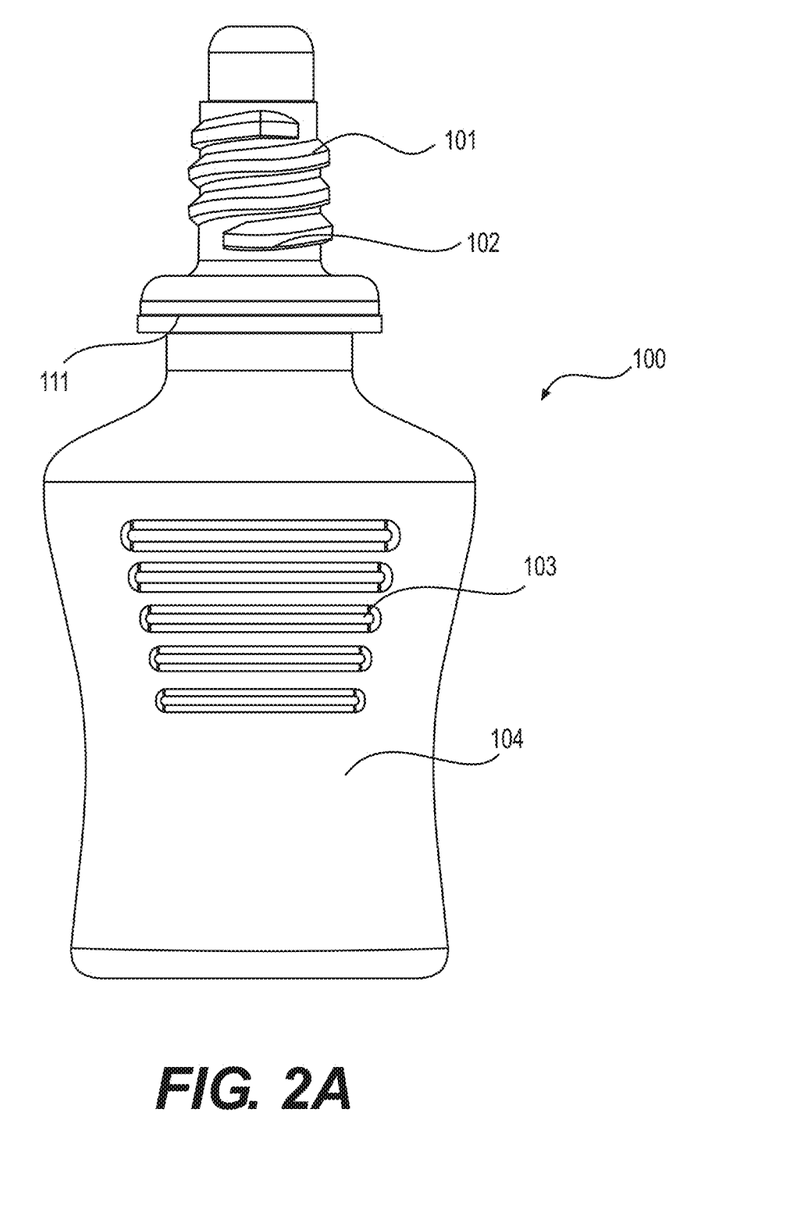
FIG. 2A is a front view of the body of a container according to an embodiment of the present invention.
Figure 2B:
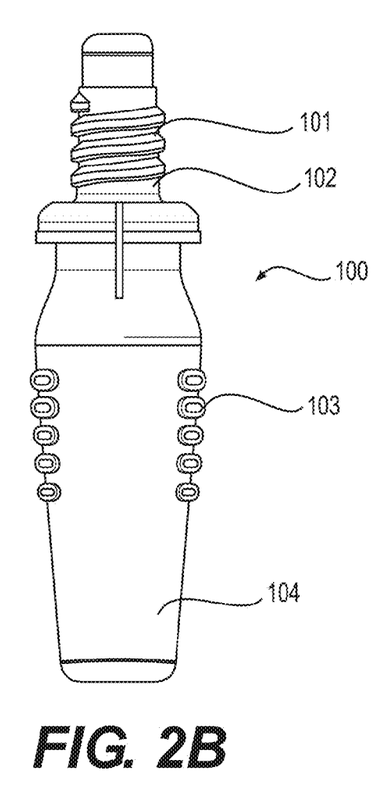
FIG. 2B is a side view of the body of the container of FIG. 2A.
Figure 2C:
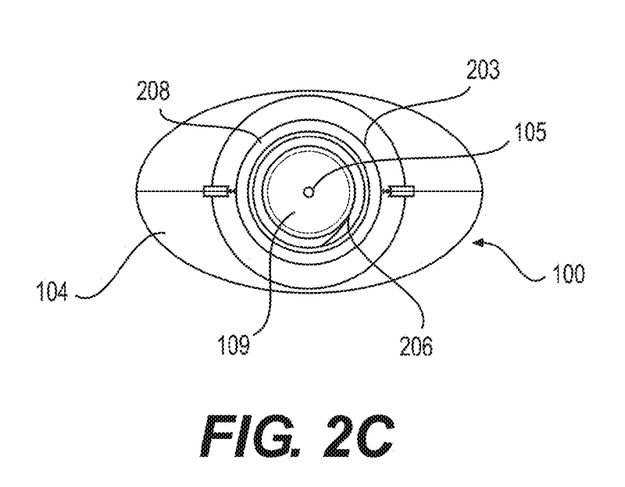
FIG. 2C is a top view of the body of a container of FIGS. 2A-2B.

As shown in FIGS. 2A-2C, container body 100 includes an upper portion that forms a neck 102 and a lower portion 104. Upper and lower portions 102 and 104 of container body 100 define a storage compartment for storing a liquid substance. The neck 102 of container body 100 is provided with structure, such as threads 101, for releasably engaging cap 200 with neck 102. Container body 100 is provided with a frangible seal 109 to seal the liquid substance in the storage compartment. The upper portion of container 100 may also be provided with a flange 111 for the purpose of providing a stop to position cap 200 in a desired position on neck 102.

For ease of handling, at least part of lower portion 104 of container body 100 may be provided with a structure that facilitates gripping of lower portion 104, such as protrusions 103 or recesses in the surface thereof. The gripping structure may form a design pattern for aesthetic purposes. In one embodiment, the design pattern is a set of parallel stripes formed by protrusions 103. Any suitable structure for facilitating gripping of container 1 may be used in the present invention.

The storage compartment of lower portion 104 may be any suitable shape or configuration, but preferably lower portion 104 is formed in the shape of a bottle, as shown in FIGS. 2A-2B. Lower portion 104 is provided with sufficient flexibility to allow the user to deform lower portion 104 by application of force to thereby propel the liquid substance through the ruptured frangible seal 109. In some embodiments, such as when the container is to be used for dispensing of relatively low viscosity liquid substances which are capable of flowing through ruptured frangible seal 109 solely under the influence of gravity, the lower portion 104 may be fabricated as a rigid structure.

Container body 100 of the single use container may be an integral, sealed structure. For dispensing the contents of the container 1, a breach 105 is made in frangible seal 109 and the liquid substance stored in the storage compartment of lower portion 104 can be released or propelled out of the storage compartment via the breach 105 in frangible seal 109 and neck 102 to cap 200.

The neck 102 has a means or structure for engaging cap 200. The present invention envisions any suitable engaging means capable of engaging neck 102 with cap 200. One such mean is threads 101 on the outer surface of the neck 102 as shown in FIGS. 2A-2C. Other suitable structures such as a friction fit, snap fit or other engaging means which provide a seal between cap 200 and neck 102 to prevent fluid from leaking may be employed.

The frangible seal 109 may be of any suitable size. Breach 105 in frangible seal 109 may be sized for dispensing the liquid substance stored in the storage compartment 104, and its size may be adjusted for the viscosity of the liquid substance, based on the rate at which it is desirable to dispense the liquid substance or a combination thereof. As a general rule, the size of breach 105 may be increased when the viscosity of the liquid substance increases. Other properties of the liquid substance may also influence the selection of the desired size of breach 105 in frangible seal 109. If the liquid substance is to be dispensed in only small quantity or slowly, then breach 105 in frangible seal 109 may be relatively small. One the contrary, when the liquid substance is to be dispensed in a large quantity or quickly, breach 105 in frangible seal 109 is preferably relatively larger in size.

The body 100 of the container of the present invention may be made of any suitable materials known to a skilled person, but typically body 100 is made from a thermoplastic material. Body 100 may be made from various flexible materials, including various plastics. For example, body 100 can be made from low density polyethylene (LDPE), high density polyethylene (HDPE) and polypropylene (PP). The materials employed to construct body 100 may be transparent or opaque. A transparent body 100 would allow the contents of the container to be visually inspected and allow the level of the dispensed substance in the container to be visually verified during dispensing.

Cap 200 may be made from the same or different material as body 100. Cap 200 includes a lower portion 202 adapted to engage with neck 102 of container body 100. Cap 200 also includes an upper portion 201 adapted for receiving applicator 300. Upper portion 201 of cap 200 forms a recess 203 at its top that is adapted to receive the applicator 300 by providing a recess 203 of the required size and shape to house applicator 300. Upper portion 201 of cap 200 may also be provided with a gripping means 210 such as protrusions, ridges, a roughened surface or recesses in the surface.

In some embodiments, applicator 300 is retained in recess 203 by a suitable retaining means. For example, applicator 300 may be glued in recess 203, may be sized to provide a friction fit between applicator 300 and recess 203, or recess 203 may be provided with an upper lip 206 located around the periphery of recess 203 and above applicator 300 when positioned in recess 203, to retain applicator 300 in recess 203. Other suitable mechanisms known a skilled person may be used to retain applicator 300 in the recess 203, such as frictional means, crimping and various retainer clips. Applicator 300 may also be affixed to surface 208 using hot-melt techniques or other fusion methods. Combinations of two or more of these retaining means may also be employed.

Figure 3:
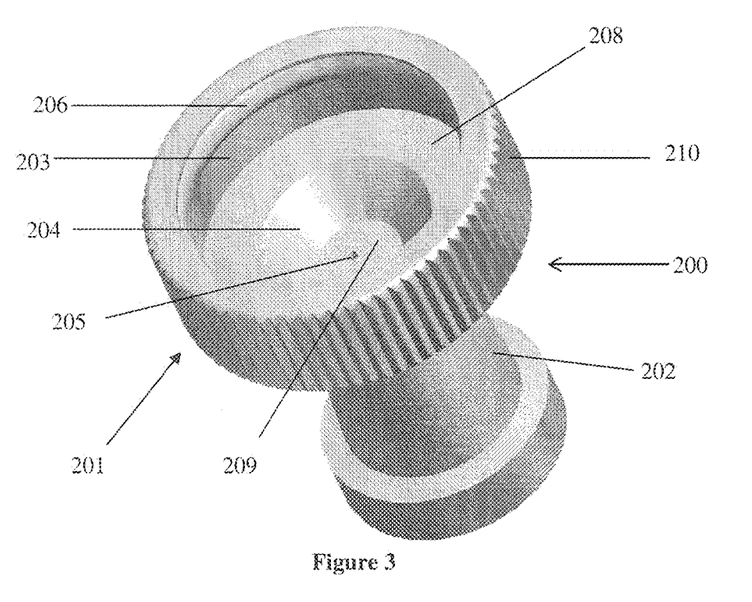
FIG. 3 depicts a cap of a container according to an embodiment of the present invention.

In the embodiment of FIG. 3, recess 203 defines a surface 208 upon which applicator 300 rests or to which applicator 300 may be glued or bonded. When applicator 300 is positioned on surface 208 a chamber 204 is defined as between the bottom of applicator 300 and lower surface 209 of chamber 204.

Chamber 204 may absorb the hydraulic shock if the liquid substance is propelled at relative high velocity through frangible seal 109. Chamber 204 allows the dispensed liquid substance to spread out and may be used to dissipate energy from the fluid caused by passing the fluid through the narrow frangible seal 109 at a relatively high velocity. Chamber 204 also allows the liquid to spread out over a significant portion of the surface area of the bottom of applicator 300 to facilitate delivery of the liquid to applicator 300.

Chamber 204 should be sufficiently large to provide a reservoir to accommodate a volume of liquid substance when the liquid substance is delivered to chamber 204. If chamber 204 is too small, the liquid substance tends may pass through or past the applicator 300, without sufficient or desirable spreading of the fluid over the surface of applicator 300. If chamber 204 is too large, it is possible for the liquid substance in the chamber 204 to achieve such a low-pressure state that it does not pass into applicator 300.

Figure 4:
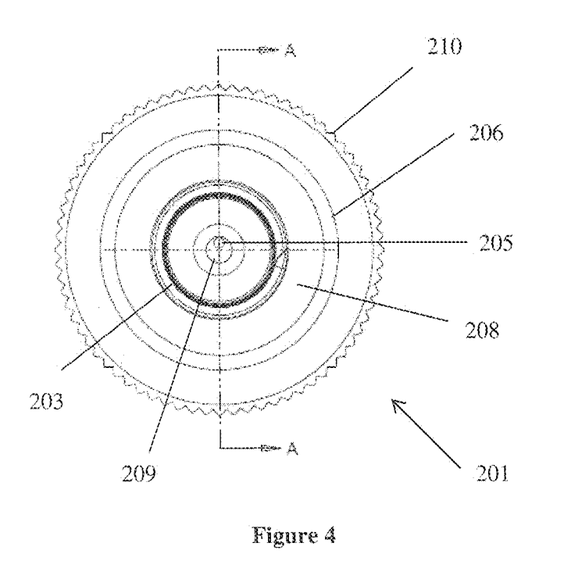
FIG. 4 is a top view of the cap of FIG. 3.

Referring to FIG. 4, a top view of cap 200 and recess 203 is shown. A channel 205 starts from lower surface 209 of chamber 204 at a location offset from the central axis of the container (the central axis 214 of the container being located at the point where the two perpendicular dotted lines cross as shown in FIG. 4) and passes through spike 207 of cap 200. Channel 205 is preferably offset from the center so that it can traverse the length of spike 207 without interfering with the piercing tip 212 of spike 207.

Figure 5:
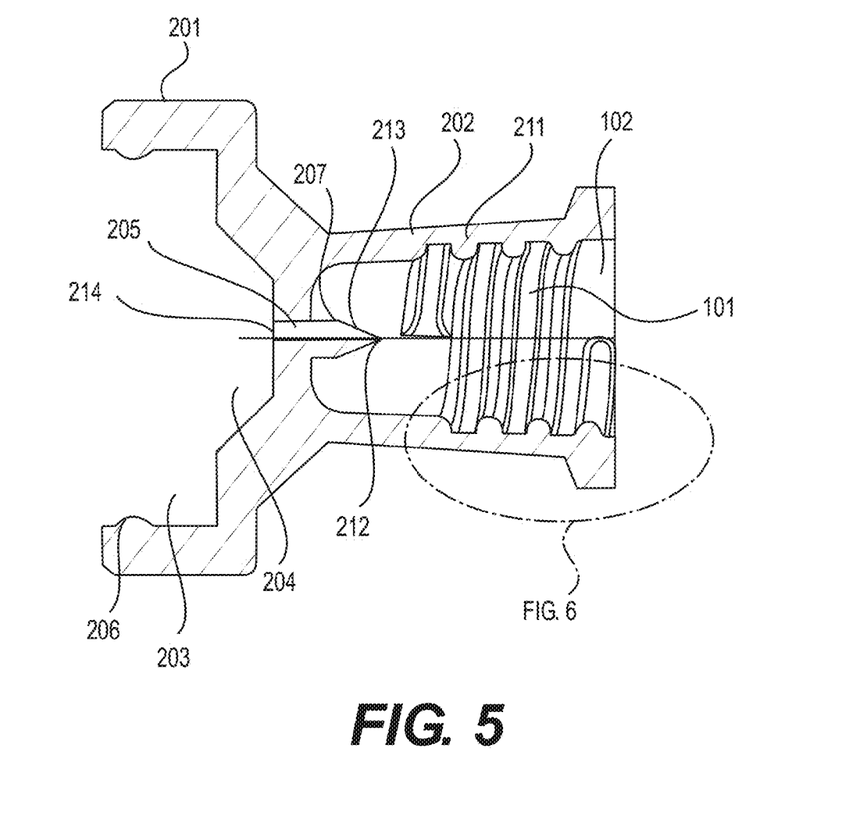
FIG. 5 is a cross-sectional view of the cap taken along line A-A of FIG. 4 when the cap is engaged with the upper portion of the container of FIGS. 2A-2C.
Figure 6:
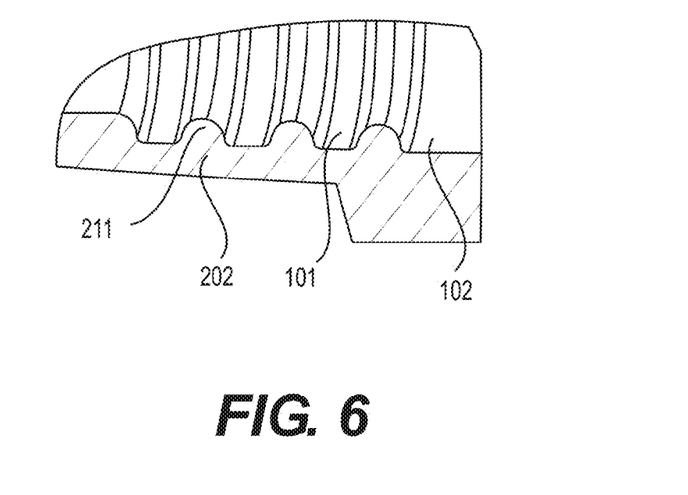
FIG. 6 is an enlarged view of the portion of the cap and container indicated in FIG. 5.

FIGS. 5-6 depict cross-sectional views of cap 200 engaged with neck 102 in the dispensing position. FIGS. 5-6 show that lower portion 202 of cap 200 includes mating threads 211 adapted to engage threads 101 of neck 102. Upper portion 201 of cap 200 is provided with is a spike 207 protruding downwards toward lower portion 202. Spike 207 includes a piercing tip 212 adapted to pierce frangible seal 109. In operation, as cap 200 is screwed onto neck 102 spike 207 pierces and breaches frangible seal 109. Spike 207 includes a tapered portion 213 to help ensure that spike 207 completely fills the pierced opening in frangible seal 109, such that the liquid substance will not leak between spike 207 and frangible seal 109. To facilitate this, frangible seal 109 may be made from a material which is adapted to seal around spike 107, such as an elastic material.

Channel 205 runs through spike 207 at a location offset from central axis 214 as shown in FIG. 5. Channel 205 may have any suitable cross-sectional shape such as circular, oval, triangular, square, rectangular, pentagon or hexagon, with circular being the preferred shape. Channel 205 exits from spike 207 through tapered portion 213 in the vicinity of piercing tip 212 at a location that ensures that the end of channel 205 passes through frangible seal 109 and provides a means for egress of liquid from compartment 104 of container body 100 into chamber 204 of cap 200.

The cross-section of channel 205 may be varied according to the liquid substance and how the substance is to be dispensed. For a low viscosity liquid substance, or when the liquid substance is intended to be dispensed slowly, the cross-section of channel 205 may be relatively small to restrict flow of the liquid substance. If the viscosity of the liquid substance is high or the liquid substance is intended to be dispensed quickly, the cross-section of channel 205 may be relatively larger to facilitate passage of the liquid.

Neck 102 and lower portion 202 of cap 200 are adapted such that when cap 200 is screwed tightly onto neck 102, spike 207 has already pierced frangible seal 109 and has advanced a sufficient distance to position the opening of channel 205 at the lower end of spike 207 within compartment 104 while maintaining spike 207 at a position where tapered portion 213 engages frangible seal 109 to ensure a good seal around spike 207.

Applicator 300 is adapted to fit in recess 203 of cap 200 at a location above chamber 204. In one embodiment, the shapes of applicator 300 and recess 203 are the same and may be any desired shape such as cubical, cylindrical, trapezoidal and the like. Applicator 300 of the embodiment depicted in the drawings is cylindrical.

Applicator 300 is preferably absorbent, to facilitate the flow of dispensed liquid substance into applicator 300, and to allow the user to apply the dispensed liquid substance easily, comfortably and cleanly. Those of ordinary skill in the art will recognize that various materials can be used for applicator 300. For example, applicator 300 may be constructed of porous foam pads, woven or non-woven fabrics or felts. One material used for the applicator 300 according to the present invention may be a sponge having a pore size of about 90 ppi, a density between 1.76-2.30 lbs/ft$^3$; a tensile strength of 26.0 psi; an elongation of 302%; a tear strength of up to 2.9 lbs/in; a CLD 25% R 0.34 psi; and a CLD 65% R 0.49 psi. The material may have a compression set of about 50%.

In some embodiments, applicator 300 may be a substantially porous pad, such as a foam pad. The foam pad can be constructed of many natural and synthetic materials. The foam pad should have good reservoiring or holding capacity for the liquid substance to be dispensed, as well as fast fluid release for transferring the substance to the skin upon application of pressure to applicator 300. In one embodiment, applicator 300 is a polyurethane foam pad. For example, a 100-pore-inch polyurethane foam pad works well when dispensing liquids of the consistency of hand lotion and the like. One especially useful foam pad is a product from Jacob Holm Industries of Helen, Ga., known as NORAFIN brand nonwoven spun-laced roll, which is a needle punch composite material comprising 63% lycose, 27% polypropylene and 10% polyethylene terephthalate (PET).

In preferred embodiments, applicator 300 may be made of a sponge or porous material, which may be produced by injection molding. Density of the sponge may be adjusted according to the liquid substance and how the substance is dispensed. For low viscosity liquid substances, the density of the sponge or porous material may be relatively high to allow slower movement of the liquid substance through applicator 300. If the viscosity of the liquid substance is high or the liquid substance is intended to be dispensed quickly, the density of the sponge may be relatively low to facilitate passage of the liquid substance through applicator 300.

The applicator may have a pore size of from about 60-120 ppi, or, 70-110 ppi, or 80-100 ppi, or 90 ppi. The applicator may have a density between about 1.5 and 3.0 lbs/ft$^3$, or between about 1.6 and 2.5 lbs/ft$^3$, or between about 1.76 and 2.30 lbs/ft$^3$, or between about 1.9 and 2.1 lbs/ft$^3$.

To protect the contents and to promote cleanliness, the single dose container may include an applicator cover adapted to releasably enclose applicator 300 until ready for use. Additionally or alternately, the entire container could be enclosed in a suitable packaging or sterile packaging if desired. Container body 100 and cap 200 may be packaged separately or may be packaged together within a single package either with cap 200 disengaged from neck 102 or cap 200 only partially screwed onto neck 102 such that spike 207 remains spaced from frangible seal 109.

To use the single dose container of the present invention, container body 100 and cap 200 are removed from the packaging and cap 200 is screwed tightly onto neck 102 of container body 100 to cause spike 207 to penetrate frangible seal 109 and fluidly connect channel 209 from chamber 204 to compartment 104. Container body 100 is then squeezed to exert pressure on compartment 104 which transfers the exerted pressure to the liquid forcing it through channel 209 into chamber 204. Once the liquid reaches chamber 204 it spreads out and absorbs into absorbent and/or porous applicator 300. Continued exertion of pressure on container body 100 along with the action of gravity, if the container is properly oriented, will force the liquid through to the upper surface of applicator 300 whereby it can be applied to a surface such as the skin. Applicator 300 may then be used as a tool for spreading the liquid substance onto the surface.

The single dose container is typically a relatively small, hand held device, but there are no particular restrictions on the size of the container or the amount of liquid substance that might be dispensed, other than the general considerations of size, weight, and resultant ease of use. The single use container is suitable for storing liquid substance with viscosity as low as 1 centipoise, as well as liquid substance with high viscosity in the range of thousands of centipoise.

Though the single use container of the present invention may be manufactured by any method known to a person skilled in the art, at least container body 100 is preferably manufactured by a blow-fill-seal process. Typically, the material for making container body 100 is extruded as a length of parison in the form of a vertically oriented, elongated, hollow tube between a pair of main mold halves for initially forming a container body 100 with an open top. Means are provided for maintaining the opening at the top of the length of parison in the portion of the parison extending upwardly above the main mold.

An extendable and retractable blowing assembly with a sealing mandrel and blowing nozzle is extended into the length of parison in the main mold halves to temporarily seal the opening. A gas is injected into the parison to mold the container with or without vacuum assist in the mold cavity defined by the main mold halves.

The main mold halves (or other mold members), along with the cooperating sealing mandrel on the blowing assembly, typically define a structure for molding the frangible seal on the top of container body 100.

The single dose container with dispenser according to the present invention answers a long felt need for a low cost disposable packaging for a wide array of liquid substances, which can include, by way of example and not limitation; pharmaceutical antiseptics, salves, cosmetics, ointments and creams. The containers are especially suitable for low viscosity substances. The container provides a packaging that offers convenience in storage, resistance to package breakage, better sanitation, and lower spillage or waste. Additionally, the container provides a package that allows a user to apply a small measured quantity of a substance in a controlled manner without getting it on the fingers or hands and without the necessity of using the fingers, hands or an additional implement to spread the substance.

EXAMPLE

One material used for the applicator 300 according to the present invention is the Z110CLMA sponge manufactured by Foamex. The sponge has pore size of 90 ppi, a density between 1.76-2.30 lbs/ft$^3$; a tensile strength of 26.0 psi; an elongation of 302%; a tear strength of up to 2.9 lbs/in; a CLD 25% R 0.34 psi; and a CLD 65% R 0.49 psi. A material with a compression set of 50% was also tested.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A single use container designed to store and dispense a liquid substance, comprising:
    a) a container body that defines a storage compartment for storing the liquid substance and provided with a neck including a seal positioned in the neck to seal a liquid substance in the storage compartment during storage;
    b) a cap defining a recess and being adapted for engaging the neck and including structure for piercing the seal and a channel which passes through the structure for piercing the seal to the recess;
    c) an applicator located in the recess such that the applicator and recess together define a chamber between an end of the channel and the applicator to allow liquid to flow from said channel into said chamber; and
    wherein said chamber has a perimeter measured in a horizontal plane when the container is upright, that is larger than a perimeter of the channel, also as measured in a horizontal plane when the container is upright, to allow expansion of liquid following from said channel into said chamber.

2. The single use container of claim 1, wherein the neck and cap include a mating threaded engagement structure.

3. The single use container of claim 1, wherein the container body is sufficiently flexible to allow application of pressure to deform the storage compartment to apply pressure to stored liquid substance for dispensing of the liquid substance through the channel and the applicator.

4. The single use container of claim 1, wherein the container body is made by a blow-fill-seal process.

5. The single use container of claim 1, wherein the piercing structure is adapted to fit tightly with the seal after the piercing structure pierces the seal to substantially prevent flow of pressurized liquid substance between the piercing structure and the seal.

6. The single use container of claim 5, wherein the piercing structure is tapered at its piercing end to fit tightly with the seal.

7. The single use container of claim 1, wherein the channel is offset from a central axis of the piercing structure.

8. The single use container of claim 1, wherein the applicator comprises a material selected from the group consisting of foam pads, sponge, wovens, non-wovens and felts.

9. The single use container of claim 1, wherein a density of the applicator is in the range of 1.5 and 3.0 lbs/ft$^3$.

10. The single use container of claim 1, wherein a density of the applicator is in the range of 1.6 and 2.5 lbs/ft$^3$.

11. The single use container of claim 1, wherein a density of the applicator is in the range of 1.76 and 2.30 lbs/ft$^3$.

12. The single use container of claim 1, wherein a porosity of the applicator is in the range of 60-120 ppi.

13. The single use container of claim 1, wherein a porosity of the applicator is in the range of 70-110 ppi.

14. The single use container of claim 1, wherein a porosity of the applicator is in the range of 80-100 ppi.

15. The single use container of claim 1, wherein a density of the applicator is in the range of 1.76 and 2.30 lbs/ft$^3$ and a porosity of the applicator is 90 ppi.

16. The single use container of claim 1, wherein an outlet of the channel is positioned proximate to a piercing tip of the piercing structure to ensure that the outlet of the channel is located within the seal in fluid communication with the compartment of the container body after the seal is pierced by the piercing structure.

17. The single use container of claim 16, wherein the outlet of the channel is located in a tapered portion of the piercing structure.

18. The single use container of claim 16, further comprising a stop to ensure that the cap is positioned on the neck such that the outlet of the channel is located within the seal in fluid communication with the compartment of the container body after the seal is pierced by the piercing structure.

* * * * *

UNITED STATES PATENT AND TRADEMARK OFFICE
CERTIFICATE OF CORRECTION

PATENT NO. : 9,688,444 B2  Page 1 of 1
APPLICATION NO. : 14/441783
DATED : June 27, 2017
INVENTOR(S) : Kinsman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this
Twenty-fifth Day of September, 2018

Andrei Iancu
*Director of the United States Patent and Trademark Office*